(12) United States Patent
Onishi et al.

(10) Patent No.: US 6,706,943 B2
(45) Date of Patent: Mar. 16, 2004

(54) BODY FLUID ABSORBENT PANEL

(75) Inventors: Kazuaki Onishi, Kanagaw-ken (JP); Masashi Nakashita, Kanagaw-ken (JP)

(73) Assignee: Uni-Charm Corporation, Kawanoe (JP)

( * ) Notice: Subject to any disclaimer, the term of this patent is extended or adjusted under 35 U.S.C. 154(b) by 42 days.

(21) Appl. No.: 09/978,673

(22) Filed: Oct. 18, 2001

(65) Prior Publication Data
US 2002/0049417 A1 Apr. 25, 2002

(30) Foreign Application Priority Data
Oct. 19, 2000 (JP) ........................................ 2000-319933

(51) Int. Cl.[7] .............................................. A61F 13/15
(52) U.S. Cl. ........................................ 604/366; 367/365
(58) Field of Search ................................ 604/365, 367, 604/375, 378, 379, 380, 366, 383, 385.101, 368; 428/172, 198, 296.7, 301.4, 373, 374, 375; 442/199, 200, 201, 212, 361, 362, 363, 375, 364

(56) References Cited

U.S. PATENT DOCUMENTS 4,872,870 A    10/1989  Jackson
5,486,167 A  *  1/1996  Dragoo et al. .............. 604/384

FOREIGN PATENT DOCUMENTS

GB         1408009      10/1975
GB         2061339       5/1981
WO     WO 92 02679      2/1992

* cited by examiner

Primary Examiner—Weilun Lo
Assistant Examiner—Jacqueline F Stephens
(74) Attorney, Agent, or Firm—Lowe Hauptman Gilman & Berner LLP

(57) ABSTRACT

A body fluid absorbent panel including fibers containing hydrophilic fibers by 80–100% by weight and superabsorbent polymer particles contains heat-fusible fibers which are fused to intertwine the fibers and thereby to form a three-dimensional network structure wherein the high absorption polymer particles are held between respective pairs of the adjacent fibers or bonded to the fibers by means of binder, and thereby falling off of the polymer particles can be prevented and the absorption efficiency can be improved.

11 Claims, 3 Drawing Sheets

BODY FLUID ABSORBENT PANEL

BACKGROUND OF THE INVENTION

This invention relates to a body fluid absorbent panel suitable for use in a disposable body fluid absorbent wearing article such as a diaper or a sanitary napkin.

In conventional disposable diapers or sanitary napkins, it is well known to use, as a body fluid absorbent panel thereof, an assembly comprising a body fluid absorbent core formed by a mixture of hydrophilic fibers such as fluff pulp and high absorption polymer particles and covered with a liquid-pervious sheet or with such liquid-pervious sheet and a liquid-impervious sheet.

It is always desired for such a disposable body fluid absorbent wearing article such as a diaper or a sanitary napkin to improve a liquid absorbing capacity achieved by the article and, at the same time, to minimize its thickness. The requirements may be satisfied by increasing the quantity of high absorption polymer particles. However, the high absorption polymer particles have not the absorption rate as high as that achieved by the fluff pulp In addition, it becomes difficult to maintain the polymer in a constant shape and possibility that the polymer may leak out from the article as its quantity increases since the polymer is present in the form of particles. Upon moisture absorption, the high absorption polymer particles form a gel block which can no more absorb further quantity of moisture and, in consequence, the article often can not achieve the absorption expected on the basis of the quantity of the high absorption polymer particles used by the article

SUMMARY OF THE INVENTION

In view of the problem raised when a large quantity of the high absorption polymer particles are used, it is an object of this invention to provide a body fluid absorbent panel improved so that the problems can be overcome.

According to this invention, there is provided a body fluid absorbent panel comprising a core having upper and lower surfaces one of which is covered with a liquid-pervious sheet while the other of which is covered with a liquid-pervious or liquid-impervious sheet and hydrophilic fibers and high absorption polymer particles contained between the upper and lower surfaces.

The improvement according to this invention is in that the core contains heat-fusible fibers comprising the hydrophilic fibers or hydrophobic fibers and the entire fibers forming the core are put together to form a three dimensional network structure as the heat-fusible fibers are fused at least some of spots at which the entire fibers intersect the heat-fusible fibers wherein the polymer particles have an absorption rate less than 20 seconds as measured by Vortex method and are held within the network structure by held between respective pairs of the adjacent fibers forming the network structure or bonded to the fibers by means of binder.

DETAILED DESCRIPTION OF THE PREFERRED EMBODIMENTS

Figure 1:
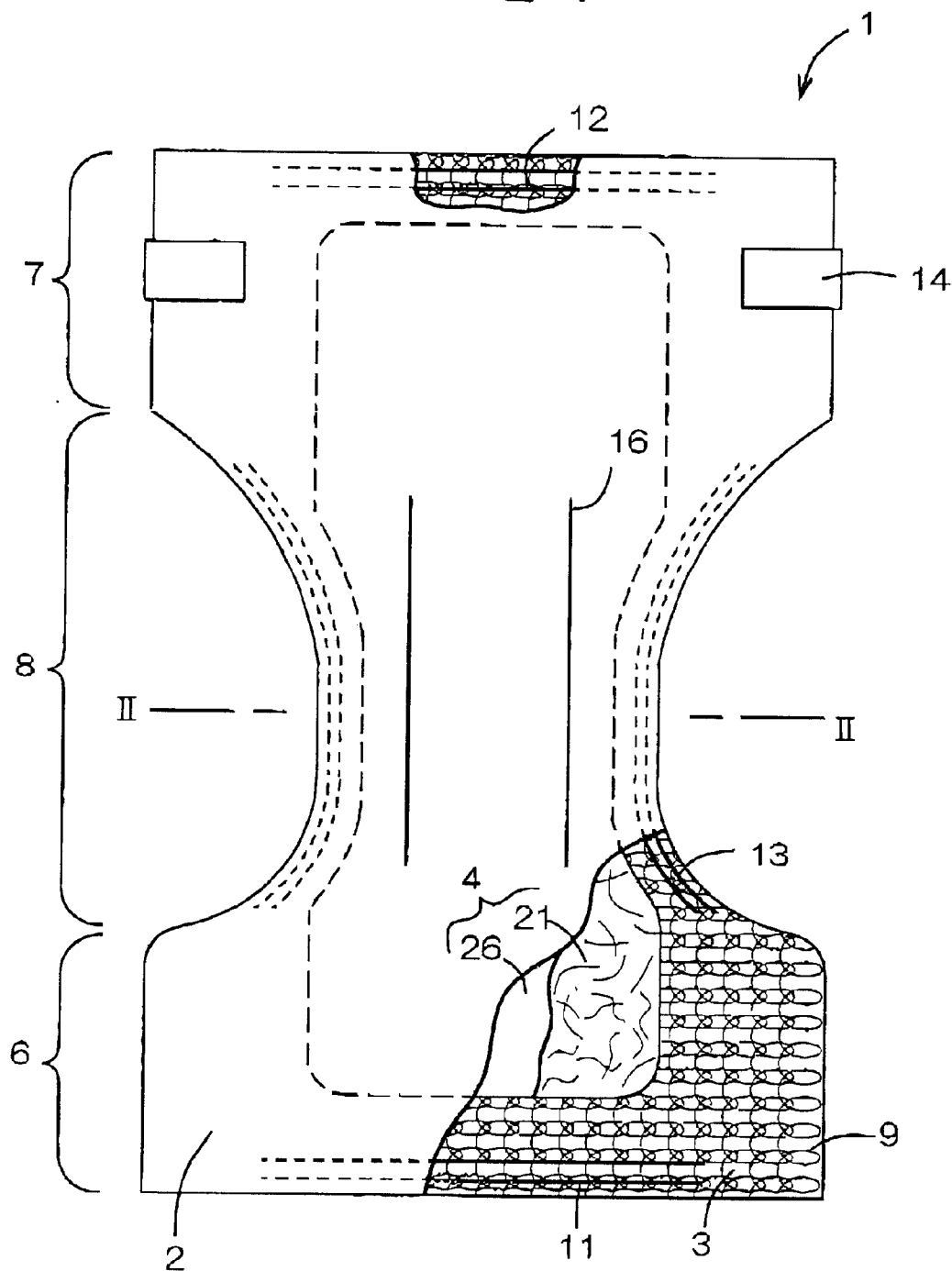
FIG. 1 is a plan view showing a disposable diaper as partially broken away.

Details of a body fluid absorbent panel according to this invention will be more fully understood from the description given hereunder with reference to the accompanying drawings FIG. 1 is a plan view showing a disposable diaper 1 using a body fluid absorbent panel according to this invention as partially broken away. The diaper 1 comprises a liquid-pervious topsheet 2 made of a nonwoven fabric or a perforate plastic film, a liquid-impervious backsheet 3 made of a plastic film and a body fluid absorbent panel 4 disposed between these two sheets 2, 3. The top- and backsheets 2, 3 extend outward beyond a peripheral edge of the panel 4 and are placed upon and water-tightly bonded to each other in these extensions by means of hot melt adhesive 9 describing a plurality of spiral curves. The diaper 1 is composed, in a longitudinal direction as viewed in FIG. 1, of a front waist region 6, a rear waist region 7 and a crotch region 8 extending between these two regions 6, 7 and along longitudinally outer end portions of the front and rear waist regions 6, 7, respectively, elastic members 11, 12 extending in a waist surrounding direction, i.e., in a transverse direction as viewed in FIG. 1 are disposed between the top- and backsheets 2, 3 and bonded under tension to the inner surface of at least one of these sheets 2, 3. Along transversely opposite side edge portions of the crotch region 8, elastic members 13 associated with respective leg-openings are disposed between the top- and backsheets 2, 3 and bonded under tension to the inner surface of at least one of these sheets 2, 3. A pair of tape fasteners 14 are attached to transversely opposite side edge portions of the rear waist region 7. The inner surface of the crotch region 8 is formed in its transversely middle zone with a pair of compressed grooves 16 extending in the longitudinal direction.

Figure 2:
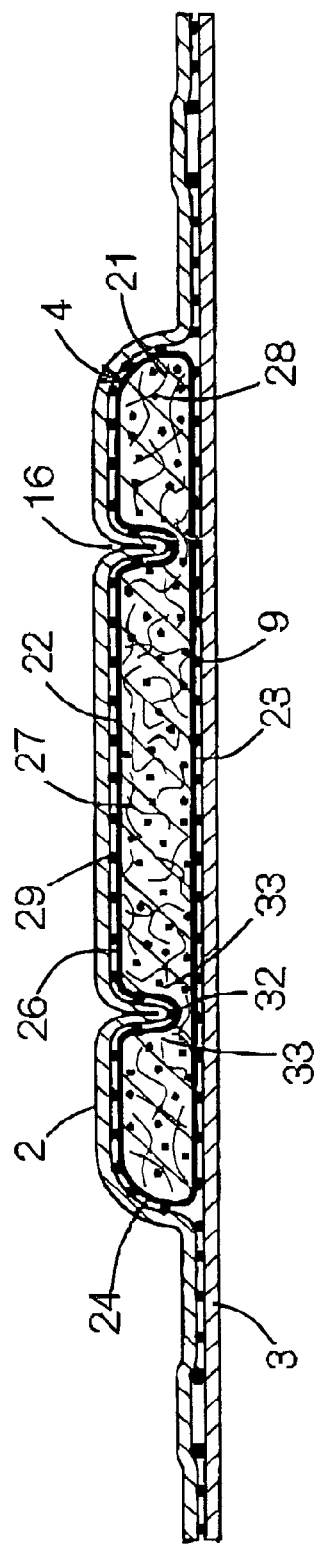
FIG. 2 is a sectional view taken along a line II—II in FIG. 1.

FIG. 2 is a sectional view taken along a line II—II in FIG. 1. The panel 4 has a core 21 and a cover sheet 26 (See FIG. 1 also) adapted to cover upper and lower surfaces 22, 23 as well as side surfaces 24 of the core 21. The core 21 comprises a plurality of fibers 27 and high absorption polymer particles 28 mixed with the fibers 27 wherein its upper surface 22 faces the topsheet 2 with the cover sheet 26 therebetween and its lower surface 23 faces the backsheet 3 with the cover sheet 26 therebetween. The core 21 may have its upper surface 22 covered with a liquid-pervious sheet and its lower surface 23 as well as its side surfaces 24 covered with a liquid-pervious or liquid-impervious sheet. In the case of the illustrated embodiment, these surfaces 21–24 are covered with the liquid-pervious cover sheet 26 in the form of tissue paper. Such cover sheet 26 is bonded to the backsheet 3 by means of hot melt adhesive 9 and bonded to the topsheet 2 by means of hot melt adhesive 29. By bonding the cover sheet 26 to the top- and backsheets 2, 3, the panel 4 is held in place and, in addition, the panel 4 is brought in close contact with the topsheet 2 so that body fluids may rapidly permeate the panel 4. The panel 4 is formed in its transversely opposite side portions with a pair of the compressed grooves 16 extending in the longitudinal direction. These compressed grooves 16 may be formed by compressing the panel 4 together with the top- and backsheet 2, 3 in a thickness direction thereof at a normal temperature or under heating until the panel 4 has a thickness along these grooves reduced to ⅔ or less, preferably to ½ or less with respect to the remaining region of the panel 4. While the length of these compressed grooves 16 in the longitudinal direction is not specified, these compressed grooves 16 preferably extend across the crotch region 8 over at least ½ of a full length of the panel 4. While a width of the respective grooves 16 at bottoms 32 thereof also is not specified, this width is preferably in a range of 0.2–5 mm. The panel 4 presents the maximum apparent density at the bottoms 32 of the respective grooves 16 at which the fibers 27 and the polymer particles 28 are compressed and a relatively high density in the vicinity of both sides 33 of the respective bottoms 32 The density of the panel 4 progressively decreases substantially in proportion to the distance from the respective grooves 16 in the transverse direction of the panel 4.

Figure 3:
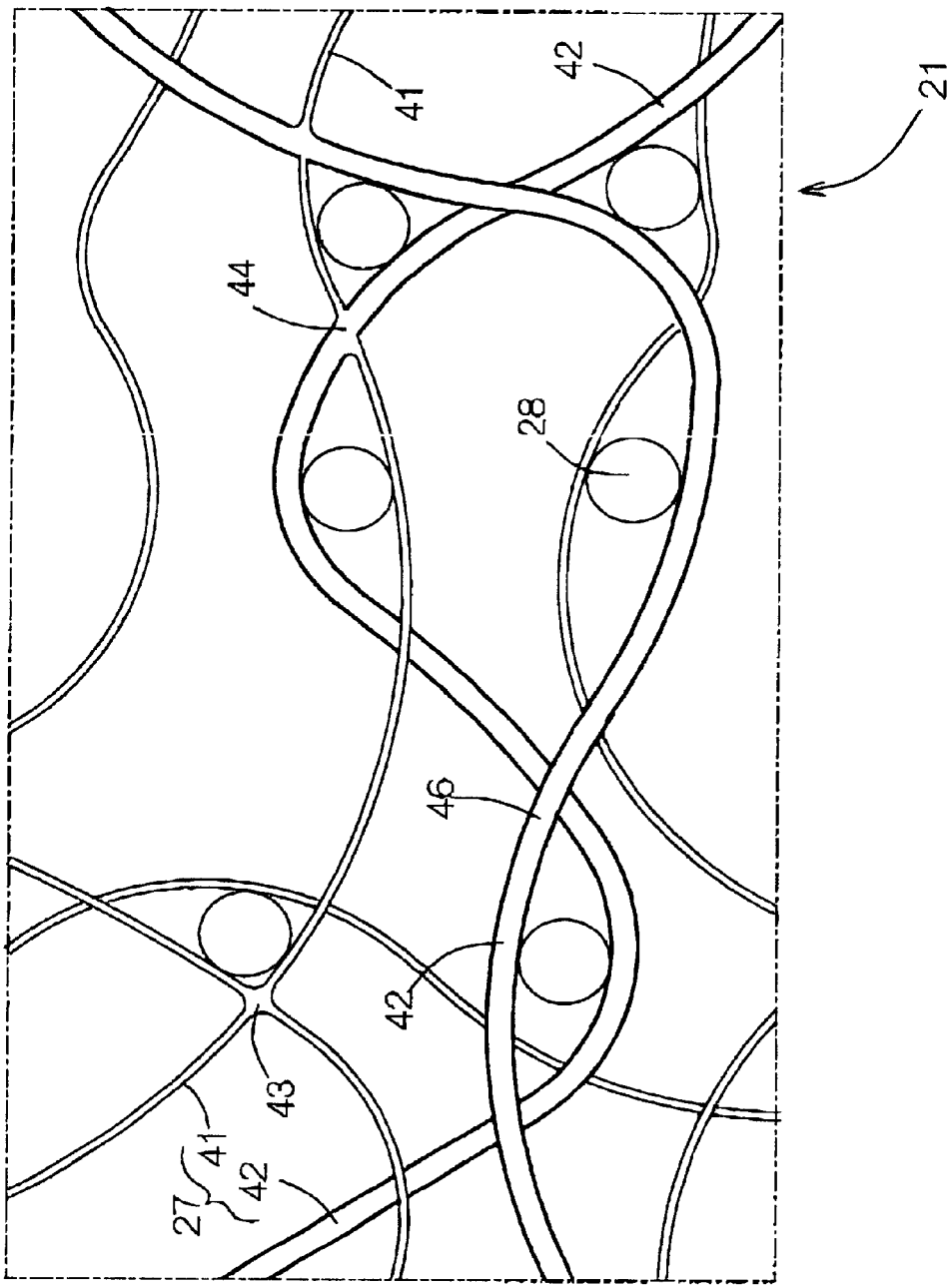
FIG. 3 is a fragmentary scale-enlarged diagram of FIG. 2.

FIG. 3 is a fragmentary scale-enlarged diagram illustrating the core 21. The core 21 is a mixture of the fibers 27 occupying 40–5% by weight of the core 21 and the high absorption polymer particles 28 wherein the fibers 27 have a basis weight of 20–100 g/m$^2$ and an apparent density in a range of 0.01–0.05 g/cm$^3$. Of the entire quantity of these fibers 27, at least 50% by weight comprises fibers having a fineness less than 6 dtex and 80–100% by weight comprises hydrophilic fibers. The fibers 27 may contain hydrophobic fibers of 20–0% by weight. Of the entire quantity of these fibers 27, 20–100% by weight comprises heat-fusible fibers which may be hydrophilic or hydrophobic. The fibers 27 may comprise at least two types of fiber having melting points different from each other and preferably comprise two or three types of fiber presenting a differential melting point at least in a range of 50° C. It is also possible to use crimped or non-crimped side-by-side or sheath-and-core type composite fibers as the fibers 27.

In the case of the core 21 exemplarily illustrated in FIG. 3, the fibers 27 comprise low melting point (i.e., 130° C.) polyethylene fibers 41 having a fineness of 2 dtex and treated to become hydrophilic and high melting point (i.e., 250° C.) polyester fibers 42 having a fineness of 4 dtex and treated to become hydrophilic. The low melting point fibers 41 occupy 70% by weight and the high melting point fibers 42 occupy 30% by weight of the entire quantity of the fibers 27. At first spots 43 at which the low melting point fibers 41 intersect one another, the low melting point fibers 41 are fused together and at second spots 44 at which the low melting point fibers 41 intersect the high melting point fibers 42, only the low melting point fibers 41 are molten and welded to the high melting point fibers 42. At third spots 46 at which the high melting point fibers 42 intersect together, these fibers 42 merely come in contact with one another but not welded together. At the first intersecting spots 43, the low melting point fibers 41 are rather firmly fused together, at the second intersecting spots 44, the low melting point fibers 41 are welded to the high melting point fibers 42 rather moderately and at the third intersecting spots 46, the high melting point fibers 42 are not welded together. Within the core 21, the superabsorbent polymer particles 28 may be held in a network structure defined by the fibers 27 in various manners. For example, the polymer particles 28 may be held between each pair of the adjacent low melting point fibers 41, 41, between each pair of the adjacent low melting point fiber 41 and high melting point fiber 42 or between each pair of the adjacent high melting point fibers 42, 42 so far as the polymer particles 28 can be held apart from one another. In addition to these manners in which the polymer particles 28 are held by the fibers 27, it is also possible to use the well known binder by means of which the polymer particles 28 are bonded to the fibers 27 comprising the low melting point fibers 41 and the high melting point fibers 42. While the well known polymer particles 28 may be used, those having a grain size of 100–1000µ and a saline retention capacity of at least 20 g/g is preferably used. 20–100% by weight of the polymer particles 28 preferably presents an absorption rate less than 20 seconds, more preferably presents an absorption rate less than 10 seconds as measured by Vortex method according to JIS K 7224. While the spherical polymer particles 28 are illustrated, preferably the surface of the individual polymer particles 28 is formed with a plurality of irregularities and thereby the surface area thereof is maximized so far as the total weight of the polymer particles 28 is maintained constant. The irregularities formed on the spherical surface of the individual polymer particles 28 facilitate the polymer particles 28 to be caught by the fibers 27 and thereby eliminate an anxiety that the polymer particles 28 might fall off from the core 21 The surface area of the individual polymer particles 28 enlarged by the irregularities serves to improve the absorption rate. A specific surface area of the polymer particles 28 functioning in this manner is preferably at least 0.03 m$^2$/g, more preferably at least 0.07 m$^2$/g as measured using AUTOPORE III9420 of Micrometrics Corp.

In such diaper 1, the quantity of water having permeated through the topsheet 2 and the cover sheet 26 into the core 21 is absorbed not only by the hydrophilic fibers contained in the fibers 27 but also by the high absorption polymer particles 28 as this quantity of water flows through the interstices of the fibers 27 forming the network structure. Of the polymer particles 28, those held between respective pairs of the adjacent low melting point fibers 41 and high melting point fibers 42 are swollen and deformed as they absorb water The polymer particles 28 swollen and deformed in this manner separate the fibers 41, 42 one from another at the second spots 44 and are relieved of the constraining effect by these fibers 41, 42. Now the polymer particles 28 can further quantity of water. A plurality of polymer particles 28 are held by the fibers 27 so that the individual polymer particles 28 may be spaced one from another. Such arrangement eliminates an apprehension that these polymer particles 28 might mutually prevent them from being swollen and form the gel block retarding permeation of water into the core 21. When at least 20% by weight of the polymer particles 28 has the absorption rate less than 20 seconds as measured by the Vortex method, the quantity of water flowing through the interstices of the fibers 27 can be rapidly caught by the polymer particles 28 and any possibility that any quantity of such water might leak out from the diaper 1. Conventionally, the polymer particles 28 have sometimes fallen off from the core 21 as the diaper 1 is handled. However, with the arrangement in which the polymer particles 28 move sideways before falling off thereof, the presence of the compressed grooves 16 function to prevent such movement of the polymer particles 28 and thereby to eliminate a possibility that the polymer particles 28 might leak out from the lateral portions of the panel 4.

The compressed grooves 16 serve also to dam up sideway flow of water in the core 21 and thereby to prevent water from leaking sideways in the diaper 1. Placement as well as length of the compressed grooves 16 are not limited to those in the illustrated embodiment and may be appropriately modified. It is even possible without departing from the scope of this invention to provide the panel 4 having none of the compressed grooves 16. It is also possible to replace the compressed grooves 16 each continuously extending in the longitudinal direction as in the illustrated embodiment by a plurality of longitudinally intermittent but substantially ribbon-like compressed regions The compressed grooves 16 formed by compressing the panel 4 together with the top- and backsheets 2, 3 as in the illustrated embodiment may be replaced by the compressed grooves 16 formed by compressing the panel 4 alone. The compressed grooves 16 obtained by compressing the core 21 under heating is advantageous in that the fibers 27 are fused together at the bottoms 32 and in the vicinity 33 thereof of the respective grooves 16. As a result, sideway movement of the polymer particles 28 and water can be reliably prevented.

The panel 4 according to this invention can be used not only for the diaper 1 as illustrated but also the other disposable body fluid absorbent wearing articles such as a sanitary napkin. In these articles, the cover sheet 26 may be formed, instead of the tissue paper, with the liquid-pervious topsheet 2 (See FIG. 1) and the liquid-impervious backsheet 3. In this case, the upper surface 22 and the lower surface 23 of the panel 4 are covered with the topsheet 2 and the backsheet 3, respectively. The absorption rate measured by Vortex method is represented by a time required for the high absorption polymer particles of 2.0 g to absorb 50 g of 0.9% physiological saline solution. The water retention of the high absorption polymer particles 28 is represented by a weight of the particles 28 of 1 g after the particles 28 have been immersed in 1 liter of 0.9% physiological saline solution for 1 hour, then water-drained for 15 minutes and finally centrifuged at 850 rpm for 90 seconds.

The body fluid absorbent panel according to this invention is constructed so that the high absorption polymer particles are held apart from one another within the core of network structure formed by the heat-fusible fibers. Such a unique arrangement enables the problem accompanied by the prior art such that the polymer particles might leak out from the panel to be solved The polymer particles in such state are free from an apprehension that the gel block might be formed and deteriorate the absorption efficiency of the panel. Such panel enables a large quantity of the high absorption polymer particles to be effectively used and to offer the absorption efficiency expected on the basis of the quantity of the polymer particles actually used.

What is claimed is:

1. A body fluid absorbent panel, comprising:
   a first sheet which is liquid-pervious and a second sheet; and
   a core disposed between said first and second sheets, said core comprising component fibers defining a three dimensional network structure and absorbent polymer particles distributed in said network structure;
   wherein:
      said polymer particles are contained within said network structure by being held between adjacent said component fibers or bonded to said component fibers;
      said component fibers comprise first fibers of a lower melting point and second fibers of a higher melting point;
      said network structure has first spots at which said first fibers are fused together, and second spots at which said first fibers are fused to said second fibers; and
      bonds between said first fibers at said first spots are stronger than bonds between said first and second fibers at said second spots.

2. The body fluid absorbent panel according to claim 1, wherein at least some of said component fibers are hydrophilic fibers; and the first fibers comprise said hydrophilic fibers or hydrophobic fibers.

3. The body fluid absorbent panel according to claim 2, wherein said polymer particles have an absorption rate less than 20 seconds as measured by the Vortex method.

4. The body fluid absorbent panel according to claim 1, wherein said component fibers contained in said core have a basis weight of 20~100 g/m$^2$.

5. The body fluid absorbent panel according to claim 1, wherein separation of said first fibers from said second fibers at said second spots is caused by swelling and deformation of said polymer particles as said polymer particles absorb a liquid.

6. The body fluid absorbent panel according to claim 1, wherein said core is compressed in a thickness direction of said core along a line spaced inwardly from a peripheral edge of said core to form a high density zone.

7. The body fluid absorbent panel according to claim 1, wherein the first and second sheets comprise tissue paper.

8. The body fluid absorbent panel according to claim 1, wherein the first and second sheets comprise a liquid-pervious topsheet and a liquid-impervious backsheet, respectively, of a disposable diaper or a sanitary napkin.

9. The body fluid absorbent panel according to claim 1, wherein said core comprise hydrophilic fibers of 5~40% by weight and said polymer particles of 60~95% by weight.

10. A body fluid absorbent panel, comprising:
    a first sheet which is liquid-pervious;
    a second sheet which is liquid-pervious or liquid-impervious; and
    a core having upper and lower surfaces one of which is covered with the first sheet while the other is covered with the second sheet, said core comprising component fibers defining a three dimensional network structure and superabsorbent polymer particles distributed in said network structure;
    wherein:
       at least some of said component fibers are hydrophilic fibers;
       said component fibers comprise a first group of fibers and a second group of fibers, the fibers of said first group intersecting each other and the fibers of said second group at a plurality of intersections at which the fibers of said first group are fused;
       the fibers of said first group comprise said hydrophilic fibers or hydrophobic fibers;
       said polymer particles have an absorption rate less than 20 seconds as measured by the Vortex method, and are contained within said network structure by being held between adjacent said component fibers or bonded to said component fibers by a binder; and
       a water retention coefficient of said polymer particles is at least 20 g/g.

11. A body fluid absorbent panel, comprising:
    a first sheet which is liquid-pervious;
    a second sheet which is liquid-pervious or liquid-impervious; and
    a core having upper and lower surfaces one of which is covered with the first sheet while the other is covered with the second sheet, said core comprising component fibers defining a three dimensional network structure and superabsorbent polymer particles distributed in said network structure;
    wherein:
       at least some of said component fibers are hydrophilic fibers;
       said component fibers comprise a first group of fibers and a second group of fibers, the fibers of said first group intersecting each other and the fibers of said second group at a plurality of intersections at which the fibers of said group are fused;
       the fibers of said first group comprise said hydrophilic fibers or hydrophobic fibers;
       said polymer particles have an absorption rate less then 20 seconds as measured by the Vortex method, and are contained within network structure by being held between adjacent said component fibers or bonded to said component fibers by a binder; and
       a specific surface area of said polymer particles is at least 0.03 m$^2$/g.

* * * * *